United States Patent
Arnold et al.

(10) Patent No.: US 9,333,351 B2
(45) Date of Patent: May 10, 2016

(54) NEUROSTIMULATION METHOD AND SYSTEM TO TREAT APNEA

(71) Applicant: Pacesetter, Inc., Sunnyvale, CA (US)

(72) Inventors: Edith Arnold, San Francisco, CA (US); Kritika Gupta, Mumbai (IN); Edward Karst, Los Angeles, CA (US); Allen Keel, San Diego, CA (US); Yelena Nabutovsky, Mountain View, CA (US); Riddhi Shah, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 145 days.

(21) Appl. No.: 14/108,161

(22) Filed: Dec. 16, 2013

(65) Prior Publication Data

US 2015/0165200 A1 Jun. 18, 2015

(51) Int. Cl.
*A61N 1/36* (2006.01)

(52) U.S. Cl.
CPC .......... *A61N 1/3611* (2013.01); *A61N 1/36139* (2013.01)

(58) Field of Classification Search
CPC ........................... A61N 1/3601; A61N 1/3611
USPC ........................................................ 607/42
See application file for complete search history.

(56) References Cited

U.S. PATENT DOCUMENTS

| | | | |
|---|---|---|---|
| 7,155,278 B2 | 12/2006 | King et al. | |
| 7,212,110 B1 | 5/2007 | Elghandout et al. | |
| 7,228,179 B2 | 6/2007 | Campen et al. | |
| 8,002,553 B2 | 8/2011 | Hatlestad et al. | |
| 8,308,661 B2 | 11/2012 | Miesel et al. | |
| 8,337,431 B2 | 12/2012 | Heruth et al. | |
| 9,054,436 B2 | 6/2015 | Boogaard et al. | |
| 2005/0209511 A1 | 9/2005 | Heruth et al. | |
| 2005/0209512 A1 | 9/2005 | Heruth et al. | |
| 2005/0209513 A1 | 9/2005 | Heruth et al. | |
| 2005/0209643 A1 | 9/2005 | Heruth et al. | |
| 2005/0215847 A1 | 9/2005 | Heruth et al. | |
| 2005/0215947 A1 | 9/2005 | Heruth et al. | |
| 2005/0222522 A1 | 10/2005 | Heruth et al. | |
| 2005/0234518 A1 | 10/2005 | Heruth et al. | |
| 2006/0170486 A1 | 8/2006 | Tranchina et al. | |
| 2006/0259098 A1 | 11/2006 | Erickson | |
| 2007/0123758 A1 | 5/2007 | Miesel et al. | |
| 2008/0312548 A1* | 12/2008 | Hartley et al. | 600/534 |
| 2009/0326608 A1 | 12/2009 | Huynh et al. | |
| 2010/0274106 A1 | 10/2010 | Heruth et al. | |

FOREIGN PATENT DOCUMENTS

EP  1 732 436 B1  4/2010
WO  01/93953 A1  12/2001

* cited by examiner

*Primary Examiner* — Amanda Patton
*Assistant Examiner* — Philip C Edwards
(74) *Attorney, Agent, or Firm* — Theresa A. Raymer (57) ABSTRACT

Methods and systems are provided to deliver a neural stimulation therapy to treat apnea episodes. The methods and systems detect a respiratory pattern of a patient and identify a type associated with the respiratory pattern. A sleep stage is detected that the patient is experiencing and the method and system identify when the sleep stage warrants therapy. When the respiratory pattern corresponds to an apnea episode (AE) and the sleep stage warrants therapy, the methods and systems deliver an apnea episode terminating neuro-stimulation (AET-NS) therapy configured to terminate the AE. A type of AE therapy that is delivered may be based on the sleep stage that was detected. The methods and systems may determine whether the AET-NS therapy successfully terminated the AE, and, if not, adjust the AET-NS therapy and deliver a new AET-NS therapy.

19 Claims, 6 Drawing Sheets

NEUROSTIMULATION METHOD AND SYSTEM TO TREAT APNEA

FIELD OF THE INVENTION

Embodiments of the present invention generally relate to neurostimulation systems and methods, and more particularly to a neurostimulation method and system to treat apnea based on sleep stage.

BACKGROUND OF THE INVENTION

Sleep apnea is a serious condition in which normal, consistent breathing during sleep is interrupted by either the complete cessation of, or significant reduction in, breathing for a few seconds (e.g., at least 10 seconds) or as long as a few minutes. Sleep apnea affects 4-6% of the general adult population and is even more common in persons with cardiovascular disease. Sleep apnea can lead to or exacerbate many serious health conditions, such as hypertension, heart failure, and pulmonary hypertension.

A common treatment used today for obstructive sleep apnea is continuous positive airway pressure (CPAP) which uses a blower to maintain elevated pressure that holds the patient's airway open. The CPAP device connects through a tube to a mask that is sealed over the patient's nose and mouth while sleeping. However, some patients find the therapy to be uncomfortable and noisy Alternative treatments for obstructive sleep apnea include a variety of mechanical devices intended to maintain a patient's upper airway, which can be unpleasant or ineffective. Another therapy for central sleep apnea is adaptive servo ventilation (ASV), which has similar user experience issues as CPAP because ASV also requires a sealed mask be placed on the patient's face.

Without treatment, sleep apnea patients may wake up repeatedly in the night. These wake-up episodes may occur at various stages of sleep. If breathing is halted for a long period of time or if the airway becomes fully blocked, the patient may wake up suddenly and completely, struggling to breathe. These episodes may be perceived as frightening by the patient, and severely limit sleep quality. In other instances, the patient may become slightly aware of limited breathing and can shift body position, temporarily to lessen the paralyzed state or take a breath without full arousal. In such cases, the patient resumes breathing easily and falls asleep again quickly.

A need remains for a device that could help patients experience the second type of episode, namely it is desirable to provide a device that would allow the patient to resume breathing without disrupting sleep completely, rather than abruptly awakening.

Neurostimulation systems (NS) are devices that generate electrical pulses and deliver the pulses to nerve tissue to treat a variety of disorders, Spinal cord stimulation (SCS) is the most common type of neurostimulation. In SCS, electrical pulses are delivered to nerve tissue in the spine typically for the purpose of chronic pain control. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Neurostimulation systems generally include a pulse generator and one or more leads. A stimulation lead includes a lead body of insulated material that encloses wire conductors. The distal end of the stimulation lead includes multiple electrodes that are electrically coupled to the wire conductors. The proximal end of the lead body includes multiple terminals, which are also electrically coupled to the wire conductors that are adapted to receive electrical pulses. The distal end of a respective stimulation lead is implanted within the epidural space to deliver the electrical pulses to the appropriate nerve tissue within the spinal cord that corresponds to the dermatome(s) in which the patient experiences chronic pain. The stimulation leads are then tunneled to another location within the patient's body to be electrically connected with a pulse generator or, alternatively, to an "extension."

Spinal cord stimulation is commonly used to treat neuropathic pain and produces a subjective sensation of numbness or tingling.

A need remains for a mechanism to treat apnea episodes without undue disruption of an individual's sleep pattern.

SUMMARY

In accordance with an embodiment, a method provides a neural stimulation therapy to treat apnea episodes. The method comprises detecting a respiratory pattern of a patient and identifying a type associated with the respiratory pattern; detecting a sleep stage that the patient is experiencing and identifying when the sleep stage warrants therapy; and when the respiratory pattern corresponds to an apnea episode (AE) and the sleep stage warrants therapy, delivering an apnea episode terminating neurostimulation (AET-NS) therapy configured to terminate the AE.

Optionally, a type of AE therapy that is delivered is based on the sleep stage that was detected. The method may further comprise determining whether the AET-NS therapy successfully terminated the AE, and adjusting the AET-NS therapy and delivering a new AET-NS therapy when a prior AET-NS therapy was not successful in terminating the AE. The method may further comprise automatically increasing the AET-NS therapy when the AET-NS therapy does not successfully terminate the AE, and/or automatically decreasing the AET-NS therapy when the AET-NS therapy causes excessive paresthesia that fully wakes up the patient.

Optionally, the method may further comprise determining whether the AET-NS therapy caused paresthesia sufficient to end the AE, but did not wake up the patient, and adjusting the AET-NS therapy based on whether the AET-NS therapy ended the AE and whether the AET-NS therapy woke up the patient. The method may further comprise providing an external device with a user input configured to permit the patient or a physician to increase and decrease the AET-NS therapy. The method may comprise downloading from an NS device to an external device at least one of a number of AE occurring in a select period of time, a duration of at least one AE, a number of times that the AET-NS therapy is delivered, a count of a success rate of the AET-NS therapy, and a history of the sleep stages in which the AET-NS therapy was delivered. The method may further comprise presenting at least one of an AE history information and AET-NS therapy history information to a patient or physician and permitting the patient or physician to adjust the AET-NS therapy based on the at least one of an AE history information and AET-NS therapy history information. Optionally, the method may iteratively adjust the AET-NS therapy in order to determine a select AET-NS therapy that induces a sufficient level of paresthesia to terminate the AE without fully awakening the patient.

In accordance with an embodiment, an external or implantable neural stimulation (NS) device is provided for treating apnea episodes. The NS device comprises a respiration sensor configured to detect a respiratory pattern of a patient and to output respiratory pattern signals; a respiration analysis (RA) module configured to determine when the respiratory pattern signals indicate an apnea episode (AE); a sleep stage (SS) sensor configured to detect a sleep stage that the patient is experiencing and to output a SS signal; a sleep state analysis (SSA) module configured to identify when the sleep stage warrants therapy based on the SS signal; and a therapy module configured to deliver an apnea episode terminating neuro-stimulation (AET-NS) therapy, when the AE is detected and the sleep stage warrants therapy, wherein the AET-NS therapy is configured to terminate the AE. The therapy module is configured to iteratively adjust the AET-NS therapy, under control of the patient or physician, in order to determine a select AET-NS therapy that induces a sufficient level of paresthesia to terminate the AE without fully awakening the patient.

Optionally, the therapy module may determine a type of AET-NS therapy to be delivered based on the sleep stage that was detected. Optionally, the respiration sensor detects a new respiratory pattern following delivery of a prior AET-NS therapy and the respiration analysis module is configured to determine whether the prior AET-NS therapy successfully terminated the AE. The therapy module is configured to adjust the AET-NS therapy and deliver a new AET-NS therapy when the prior AET-NS therapy was not successfully in terminating the AE. Optionally, the therapy module may be configured to automatically increase the AET-NS therapy when the AET-NS therapy does not successfully terminate the AE.

Optionally, the therapy module is configured to automatically decrease the AET-NS therapy when the AET-NS therapy causes excessive paresthesia that wakes up the patient. The RA module may be configured to determine whether the AET-NS therapy caused paresthesia sufficient to end the AE, and the SSA module is configured to determine when the AET-NS therapy did not wake up the patient. The therapy module is configured to adjust the AET-NS therapy based on whether the AET-NS therapy ended the AE and whether the AET-NS therapy woke up the patient. The NS device may further comprise a communications input configured to communicate with an external device. The external device has a user input configured to permit the patient or a physician to enter program information to increase and decrease the AET-NS therapy. Optionally, the NS device may further comprise a transceiver to transmit from the NS device, to an external device, at least one of a number of AE occurring in a select period of time, a duration of at least one AE, a number of times that the AET-NS therapy is delivered, a count of a success rate of the AET-NS therapy, and a history of the sleep stages in which the AET-NS therapy was delivered.

In accordance with an embodiment, an external device is provided with a display configured to present at least one of an AE history information and AET-NS therapy history information to a patient or physician and permitting the patient or physician to adjust the AET-NS therapy based on the at least one of an AE history information and AET-NS therapy history information.

DETAILED DESCRIPTION

Neurostimulation, such as spinal cord stimulation, can produce paresthesia that the patient experiences as a tingling sensation. This is typically seen as an undesirable side effect, but could also be used as a low level sensory stimulation to arouse a patient into light waking. This could help improve the sleep quality and quantity by delivering enough sensory stimulation to cause the patient to shift or stir and resume breathing, without leading to complete arousal in a struggle to breathe.

Figure 1:
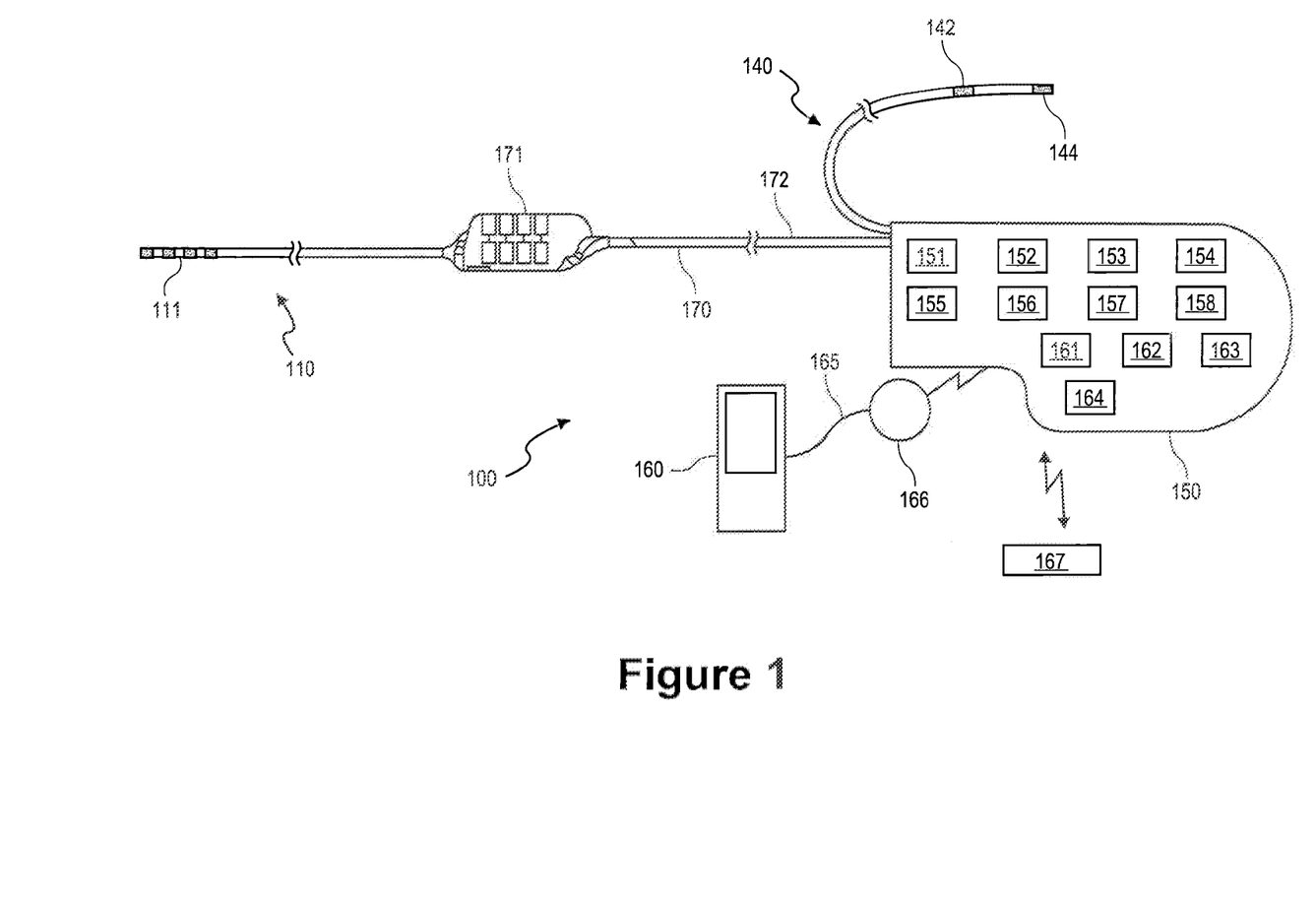
FIG. 1 depicts a neurological stimulation system that generates electrical pulses for application to nervous tissue of a patient according to one embodiment.

FIG. 1 depicts a neurological stimulation system 100 that generates electrical pulses for application to nervous tissue of a patient according to one embodiment. For example, system 100 may be adapted to stimulate spinal cord tissue, peripheral nerve tissue, deep brain tissue, cortical tissue, or any other nervous tissue within a patient's body.

System 100 includes an external or implantable NS device 150 that is adapted to generate electrical pulses for application to the nerve system of a patient. Implantable NS device 150 typically comprises a metallic housing that encloses controller 151, pulse generating circuitry 152, battery 153, recharging circuit 154, far-field and/or near field communication circuitry 155, battery charging circuitry 156, switching circuitry 157, etc. of the device. Controller 151 typically includes a microcontroller or other suitable processor for controlling the various other components of the device. Software code is typically stored in memory of the NS device 150 for execution by the microcontroller or processor to control the various components of the device.

In accordance with embodiments herein, the system 100 is configured to afford a closed-loop implantable NS device 150 that uses respiration sensors such as an accelerometer, an impedance sensor, EGM signal from an already implanted cardiac device, external motion sensor on the chest, or a satellite implantable sensor to monitor respiration. The NS device 150 monitors respiration to determine whether the user has stopped breathing and is experiencing an apnea episode (AE). The NS device 150 also includes (or communicates with) a sleep state (SS) sensor (such as an accelerometer, or an EEG or EOG monitor) to monitor a sleep state of the patient. The NS device 150 uses the sleep state to determine whether to deliver an apnea episode terminating neuro-stimulation (AET-NS) therapy to induce the paresthesia. The sleep state may be used to select between multiple options for AET-NS therapy (e.g., light or weak AET-NS therapy when in a lighter sleep state, and heavy or strong AET-NS therapy when in a deeper sleep state). When the patient stops breathing in connection with an apnea episode, the NS device 150 delivers an AET-NS therapy to produce paresthesia at one or more select segments of the patient's body. Once the AET-NS therapy is delivered, the NS device 150 may use the respiration sensor to determine whether the induced paresthesia was effective in ending the apnea episode. The sleep state sensor may also be used to determine whether the patient has reached full wakefulness following delivery of the AET-NS therapy.

The NS device 150 may adjust the neural stimulation parameters to titrate (e.g., iteratively increase or decrease) the level of induced paresthesia based on feedback to encourage a particular or select result, such as whether the prior AET-NS therapy successfully terminated the apnea episode and did not entirely arouse the patient. In accordance with at least certain embodiments, the NS device 150 is configured to achieve successful cessation of apnea episodes without causing complete arousal of the patient by iteratively looping through therapies followed by feedback regarding one or more criteria. The feedback enables a patient or physician to fine tune a therapy over one or more sleep cycles to avoid arousing the patient, such as while delivering a somatic therapy.

The NS device 150 represents an external or implantable neurostimulator that is able to produce paresthesia. For example, the NS device 150 may be a spinal cord stimulation (SCS) device and will serve as the example neurostimulator in the certain embodiments described herein. The NS device 150 includes a device that is implanted in the lower abdominal area and a multipolar lead implanted in the epidural space. Other sites for sensory stimulation, such as the brachial plexus or lumbosacral plexus, can also be stimulated by the NS device 150 and electrodes. A low-level (sub-motor threshold) sensory stimulation causing paresthesia is used to arouse a patient into a light awaking state or cause slight discomfort to the patient that may prompt the patient to breathe or change body position subconsciously without complete arousal from sleep. In an alternate embodiment, the system may cause venous pooling, alterations in limb body temperature or other sensations targeted to the entire body or a specific part of the body to cause the patient to change position or relieve paralysis of the airway in the case of an obstructive sleep apnea episode.

In the sleep apnea treatment system 100, the NS device 150 contains or communicates with one or more sensors to monitor respiration. Three examples of such sensors are an impedance sensor (Z), a photoplethysmography (PPG) sensor and a direct pressure measurement in or near the lungs, with the signal band-pass filtered around typical respiration frequencies. A further example of a sensor is an accelerometer that records rhythmic thoracic movement and physical vibrations associated with respiration. The device may have an ability to communicate wirelessly through such technology as RF with an external wearable headband EEG and optionally an EOG unit. In an alternate embodiment, the NS device 150 may communicate with another device capable of monitoring respiration, such as a patient's cardiac rhythm management (CRM) device, if present. The NS device 150 can be rechargeable and programmable by the patient or physician.

The NS device 150 may operate 24/7 or may be turned on by the patient prior to going to sleep. The NS device 150 may periodically search for communication with an EEG headband unit and become activated when that communication is established. Optionally, the NS device 150 may turn on automatically at set times or when the patient lies down or remains still for more than a set time limit. When the NS device 150 is operational, it will monitor respiration. If the respiration rate or tidal volume drops below a normal range for a sleeping individual, the NS device 150 will initiate a process to determine whether to deliver neural stimulation. Immediately following stimulation, the NS device 150 will check the respiration. If the respiration returns to normal, the NS device 150 will continue to monitor for the next episode of respiration interruption. If the respiration still indicates an apnea episode persists, this information will be logged and a different set of neural stimulation parameters (that are more likely to produce paresthesia) may be attempted during the current apnea episode or at the next apnea episode.

In another embodiment, the system 100 may use information from an external EEG or EOG sensor to target the neural stimulation to a select (e.g., optimal) stage in the sleep cycle or titrate the level of stimulation. For example, if the respiration rate or tidal volume drops below a threshold or normal range for a sleeping individual, the NS device 150 will start receiving and analyzing the output of the EEG or EOG monitor. If an EEG monitor measures predominantly theta waves (very slow brain waves that predominate in the first two sleep stages). it may be desirable to deliver an AET-NS therapy that is light or gentle (relative to other therapy options) as the patient is not in deep sleep. If the EEG monitor measures predominantly delta waves (deep, slow brain waves that predominate in the third and fourth sleep stages), it may be desirable to deliver an AET-NS therapy that is heavy or stronger (relative to other therapy options) in order to shift the patient from deep sleep to the lighter sleep stage 1 or 2, with theta waves predominating. By delivering an AET-NS therapy configured to transition the patient from a deeper sleep stage to a lighter sleep stage, the NS device 150 seeks to avoid waking up the patient with a start, feeling groggy and disoriented. Instead, the patient may not wake up, only partially wake up, or wake up feeling as if he/she weren't asleep at all. If the EEG monitor measures predominantly alpha or beta waves (higher frequency brain waves, associated with dreaming and REM sleep), it may be desirable to deliver even stronger AET-NS therapy (and associated paresthesia) to overcome the voluntary muscle paralysis that takes over when in the fourth or fifth sleep stage. Thus, the brain wave frequency band detected by the EEG monitor can help titrate the dosage (intensity and/or duration) of paresthesia.

The NS device 150 may comprise a separate or an attached extension component 170. If extension component 170 is a separate component, extension component 170 may connect with the "header" portion of NS device 150. If extension component 170 is integrated with NS device 150, internal electrical connections may be made through respective conductive components. Within NS device 150, electrical pulses are generated by pulse generating circuitry 152 and are provided to switching circuitry 157. The switching circuit connects to outputs of NS device 150. Electrical connectors (e.g., "Bal-Seal" connectors) within connector portion 171 of extension component 170 or within the NS device header may be employed to conduct the stimulation pulses.

For implementation of the components within NS device 150, a processor and associated charge control circuitry for an implantable pulse generator is described in U.S. Patent Publication No. 20060259098, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. patent Ser. No. 11/109,114, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within NS device 150. Different pulses on different electrodes may be generated using a single set of pulse generating circuitry using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO/2001/093953 A1, entitled "NEUROMODULATION THERAPY SYSTEM," which are incorporated herein by reference. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may be implanted, subcutaneous or secured to a patient's skin, and may comprise a lead body of insulation material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number of electrodes 111, terminals, and internal conductors.

As one example, the stimulation lead 110 may be implanted proximate the patient's spinal column, with the proximal end of the lead body extending through the patient's skin and configured to be connected to an external NS device 150 (e.g., only at bed time). For example, the NS device 150 may be an external device worn by the patient, similar to an insulin pump worn by diabetics, while the lead 110 is implanted at a neurostimulation site.

The NS device 150 includes one or more respiration and sleep stage inputs 161 that are configured to receive respiratory pattern (RP) and sleep stage (SS) signals. A sensing lead 140 is connected to the NS device 150. The sensing lead 140 collects respiratory pattern and/or sleep stage signals from a patient and supplies the respiratory pattern and/or sleep stage signals to the inputs 161. Optionally, the inputs 161 may also receive respiratory pattern signals and/or sleep state signals from a remote wireless monitor 167, a separate implantable device and/or from an external device. The wireless sensor 167 may represent a standalone EEG monitor or EOG monitor, such as an EEG head band placed on the patient's head to monitor brain waves. The respiratory pattern and/or sleep state signals are representative of respiratory pattern rhythms experienced by the patient over a period of time. For example, an external monitor 167 may send an analog or digital signal of the new activity signal or a signal representing a reduced information set of characteristics of respiratory pattern rhythms and/or brain wave activity. For example, the signal received at input 161 may represent a simple number or control signal containing the sleep stage encoded. For example, the monitor 167 may analyze brain wave activity or other sleep stage signals, determine the sleep stage, and output to the NS device 150 a number indicative of the sleep stage. Hence, the NS device 150 would be compatible with various types of SS monitors 167.

The sensing lead 140 includes respiration and/or sleep state sensors 142 and 144 that sense respiratory pattern and/or brain waive activity and generate respiratory pattern signals and/or sleep stage signals, respectively. As one example, the sensors 142, 144 may sense motion. Optionally, the sensing lead 140 may include sleep stage sensors configured to detect a sleep stage that the patient is experiencing and to output a sleep stage signal. The signals may represent EEG or EOG signals, IEGM signals, heart sound signals, blood pressure signals, blood oxygen content signals and any other signal that correlates to sleep stages.

The NS device 150 may include a respiration analysis (RA) module 158 that analyzes respiratory pattern signals to identify the occurrence of acceptable and unacceptable respiratory patterns. For example, as the acceptable or unacceptable respiratory pattern, the RA module 158 is configured to determine when the respiratory pattern signals indicate an apnea episode (AE). The RA module 158 may detect onset and/or termination of various respiratory pattern irregularities that are classified as different types of AE.

Alternatively, the NS device 150 may receive a communication from an external device or another implantable device indicating that onset of an AE has been detected, an AE has changed type or status, an AE has been terminated and the like. For example, the NS device 150 may receive the communication from an implantable pacemaker, ICD, CRT, defibrillator, CRM device and the like. Optionally, the NS device 150 may communicate with an external home monitor, external programmer, external ECG monitor and the like. For example, the NS device 150 may download stored or real-time information to an external home monitor, external programmer, external ECG monitor and the like. The stored or real-time information may include any of the information discussed herein, including but not limited to an AE history, AET-NS therapy information, termination results and the like. The external home monitor, external programmer, external ECG monitor may be used to program new AET-NS therapies, adjust AET-NS therapy parameters, respiratory patterns, levels of brain activity to separate sleep stages, and the like.

Optionally, the controller 151 may be configured to direct the NS device 150 to begin operation in a select one of multiple NS configurations (e.g., electrode configuration and polarity) for the AET-NS therapy in response to a determination that the respiratory pattern signals exhibits an irregular respiratory pattern. The select NS configuration may be pre-programmed or based on the type of respiratory pattern detected.

The NS device 150 includes memory 164 that is configured to save programmed parameters, such as multiple AET-NS therapy configurations, respiratory pattern parameters or templates, sleep state brain wave activity parameters or templates and the like. The memory 164 may also record and log any physiologic information collected during operation, such as AE history, therapy history, termination results and the like.

The NS device 150 includes a sleep stage analysis (SSA) module 162 that is configured to derive, from the SS signals, characteristic values (CVs) for at least one characteristic indicative of a sleep stage being experienced by the patient while the NS device operates. The SSA module 162 identifies the present sleep stage (e.g., stage 1 to stage 5) and determines when the present sleep stage warrants therapy. For example, when the patient is in a select sleep stage (e.g., stages 3 or 4 or 5), the SSA module 162 may determine that therapy is warranted, whereas when the patient is in another select sleep stage (e.g., sleep stages 1 or 2), the SSA module 162 may determine that therapy is not warranted.

The NS device 150 also includes a therapy module 163 that is configured to deliver an apnea episode terminating neurostimulation (AET-NS) therapy, when an AE is detected and when the sleep stage is determined to warrant therapy. The therapy module 163 delivers an AET-NS therapy that is configured to terminate the AE. The therapy module 163 may determine a type of AET-NS therapy to be delivered based on the sleep stage that was detected. For example, when in sleep stages 3-5, a stronger AET-NS therapy may be delivered that is configured to stimulate larger portions of the patient's body and/or deliver the AET-NS therapy with stimulation having a higher energy level (relative to other stimulation energy level options). The therapy module 163 may be configured to automatically increase the AET-NS therapy when the AET-NS therapy does not successfully terminate the AE. The therapy module 163 may be configured to automatically decrease the AET-NS therapy when the AET-NS therapy causes excessive paresthesia that wakes up the patient (e.g., when a motion sensor detects that the patient sits up, gets out of bed or otherwise moves more than a select limit). The therapy module 163 may be configured (automatically or under manual control by the physician or patient) to iteratively adjust the AET-NS therapy, under control of the patient or physician, in order to determine a select AET-NS therapy that induces a sufficient level of paresthesia to terminate the AE without fully awakening the patient.

The respiration sensors 142, 144 may detect a new respiratory pattern following delivery of a prior AET-NS therapy and the respiration analysis module 158 may determine whether the prior AET-NS therapy successfully terminated the AE. The therapy module 163 then adjusts the AET-NS therapy and delivers a new AET-NS therapy when the prior AET-NS therapy was not successful in terminating the AE.

The RA module 158 may be configured to determine whether the AET-NS therapy caused paresthesia sufficient to end the AE, and the SSA module 162 may be configured to determine when the AET-NS therapy did not wake up the patient. When this occurs, the therapy module 163 adjusts the AET-NS therapy based on whether the AET-NS therapy ended the AE and whether the AET-NS therapy woke up the patient.

The communications circuit 155 includes communications inputs/outputs (e.g., a transceiver) configured to communicate with an external device, implantable or external sensors and/or other implantable device. The external device includes a user input configured to permit the patient or a physician to enter device program parameters, through the communications circuit 155, to increase, decrease and otherwise change the AET-NS therapy. The communications circuit may include a transceiver to transmit from the NS device, to an external device, at least one of a number of AE occurring in a select period of time, a duration of at least one AE, a number of times that the AET-NS therapy is delivered, a count of a success rate of the AET-NS therapy, and a history of the sleep stages in which the AET-NS therapy was delivered.

The controller 151 changes the NS configuration by switching between at least one of i) first and second electrode combinations, ii) first and second stimulus patterns, and iii) first and second active electrode placements, utilized to delivery an AET-NS therapy from the NS lead. Optionally, the controller 151 may change the NS configuration by switching between first and second stimulus patterns utilized to delivery an AET-NS therapy from the NS lead. Optionally, the controller 151 may change the NS configuration for an AET-NS therapy by changing a value of at least one parameter from the set of configuration parameters that includes stimulus phase, frequency, pulse width, pulse amplitude, number of active electrodes, active electrode pattern, active electrode position within electrode array, active electrode placement with respect to a reference anatomy. The parameters may be programmable by the patient or physician. The controller 151 may change the NS configuration based on programmed parameters.

The AET-NS therapy may be configured to target the autonomic nervous system (ANS) and/or the somatic nervous system (SoNS). In one embodiment, the NS device 150 and controller 151 are configured to target AET-NS therapy at select segments of the SoNS. In another embodiment, the NS device 150, and controller 151, are configured to target AET-NS therapy first at a select segment(s) of the SoNS and if ineffective to then switch to or add/supplement an AET-NS therapy targeted at a select segment(s) of the ANS.

The autonomic nervous system (ANS or visceral nervous system or involuntary nervous system) is the part of the peripheral nervous system that acts as a control system, functioning largely below the level of consciousness, and controls visceral functions. The ANS affects heart rate, digestion, respiratory rate, salivation, perspiration, pupillary dilation, micturition (urination), and sexual arousal. Most autonomous functions are involuntary but a number of ANS actions can work alongside some degree of conscious control. Everyday examples include breathing, swallowing, and in some cases functions such as heart rate.

The ANS is generally divided into two subsystems: the parasympathetic nervous system (PSNS) and sympathetic nervous system (SNS), which operate independently in some functions and interact co-operatively in others. In many cases, the PSNS and SNS have "opposite" actions where one activates a physiological response and the other inhibits it. The sympathetic nervous system is a "quick response mobilizing system" and the parasympathetic is a "more slowly activated dampening system". The enteric nervous system is also sometimes considered part of the autonomic nervous system, and sometimes considered an independent system.

In general, ANS functions can be divided into sensory (afferent) and motor (efferent) subsystems. Within both, there are inhibitory and excitatory synapses between neurons. Relatively recently, a third subsystem of neurons that have been named 'non-adrenergic and non-cholinergic' neurons (because they use nitric oxide as a neurotransmitter) have been described and found to be integral in autonomic function, in particular in the gut and the lungs.

The somatic nervous system (SoNS or voluntary nervous system) represents the part of the peripheral nervous system associated with the voluntary control of body movements via skeletal muscles. The SoNS includes efferent nerves responsible for stimulating muscle contraction, including all the non-sensory neurons connected with skeletal muscles and skin. For example, there are numerous segments of nerves in the body and with each segment there is a pair of sensory and motor nerves. In the body, a portion of the segments of nerves are in the spinal cord and a portion of the segments are in the brain stem.

The Somatic Nervous System may be divided into three parts, namely i) Spinal Nerves which are peripheral nerves that carry sensory information into the spinal cord and motor commands; ii) Cranial Nerves which are the nerve fibers that carry information into and out of the brain stem (e.g., including smell, vision, eye, eye muscles, mouth, taste, ear, neck, shoulders and tongue); and iii) Association Nerves which are nerves that integrate sensory input and motor output numbering thousands.

The somatic nervous system controls all voluntary muscular systems within the body, with the exception of reflex arcs. The basic route of nerve signals within the efferent somatic nervous system involves a sequence that begins in the upper cell bodies of motor neurons (upper motor neurons) within the pre-central gyrus (which approximates the primary motor cortex). Stimuli from the pre-central gyrus are transmitted from upper motor neurons and down the corticospinal tract, via axons to control skeletal (voluntary) muscles. These stimuli are conveyed from upper motor neurons through the ventral horn of the spinal cord, and across synapses to be received by the sensory receptors of alpha motor neurons (large lower motor neurons) of the brainstem and spinal cord.

Figure 2A:
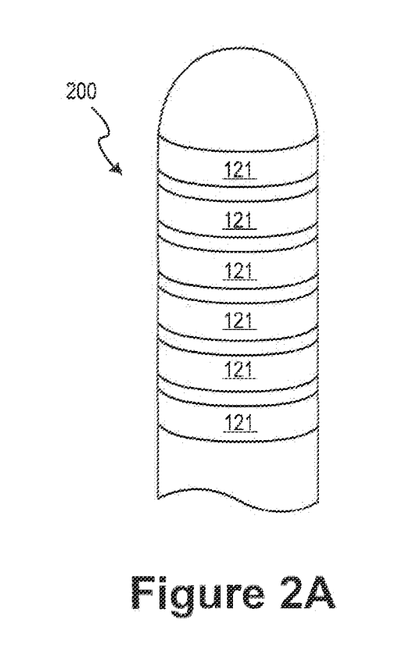
FIGS. 2A-2C respectively illustrate stimulation portions for inclusion at the distal end of a lead according to various embodiments.
Figure 2B:
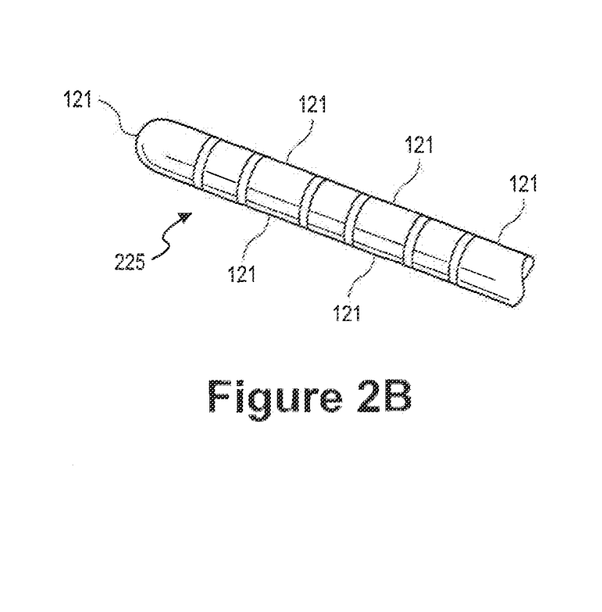
Figure 2C:
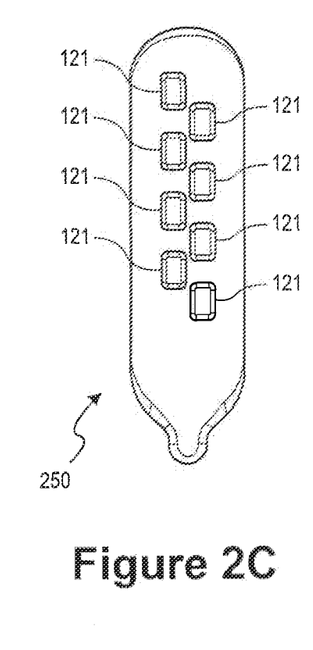

FIGS. 2A-2C illustrate stimulation portions 200, 225, and 250 for inclusion at the distal end of lead 110. Stimulation portion 200 depicts a conventional stimulation portion of a "percutaneous" lead with multiple ring electrodes. Stimulation portion 225 depicts a stimulation portion including several "segmented electrodes" 121. The term "segmented electrode" 121 is distinguishable from the term "ring electrode." As used herein, the term "segmented electrode" refers to an electrode 121 of a group of electrodes 121 that are positioned at the same longitudinal location along the longitudinal axis of a lead and that are angularly positioned about the longitudinal axis so they do not overlap and are electrically isolated from one another. Example fabrication processes are disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure.

Although not required for all embodiments, the lead bodies of lead(s) 110 and extension component 170 may be fabricated to flex and elongate in response to patient movements upon implantation within the patient. By fabricating lead bodies according to some embodiments, a lead body or a portion thereof is capable of elastic elongation under relatively low stretching forces. Also, after removal of the stretching force, the lead body is capable of resuming its original length and profile. For example, the lead body may stretch 10%, 20%, 25%, 35%, or even up or above to 50% at forces of about 0.5, 1.0, and/or 2.0 pounds of stretching force.

Controller device 160 may be implemented to battery 153 of NS device 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown).

The patient then places the primary coil 166 against the patient's body immediately above the secondary coil (not shown), i.e., the coil of the implantable medical device. Controller 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to battery 153 by recharging circuit 154. Recharging circuit 154 may also communicate status messages to controller 160 during charging operations using pulse-loading or any other suitable technique. For example, controller 160 may communicate the coupling status, charging status, charge completion status, etc. Optionally, the controller 160 may operate as a "relay" by receiving RP and/or SS signals from a separate implantable device and/or an external device and relaying/conveying the RP and/or SS signals to the NS device 150.

External controller device 160 is also a device that permits the operations of NS device 150 to be controlled by user after NS device 150 is implanted within a patient, although in alternative embodiments separate devices are employed for charging and programming. For example, the external controller device 160 may be used by the patient or physician to program the parameters for the AET-NS therapy, various AET-NS therapies to be delivered based on the respiratory pattern, various AET-NS therapies to be delivered based on the sleep stage and the like.

Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with NS device 150.

Controller device 160 preferably provides one or more user interfaces to allow the user to program, operate, download information from, and interrogate the NS device 150. The user interfaces may permit the user to move electrical stimulation along and/or across one or more stimulation leads using different electrode combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is incorporated herein by reference. Also, controller device 160 may permit operation of NS device 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. The NS device 150 modifies internal parameters in response to the control signals from controller device 160 to vary the stimulation characteristics of stimulation pulses transmitted through stimulation lead 110 to the tissue of the patient. Neurostimulation systems, stimsets, and multistimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Figure 3:
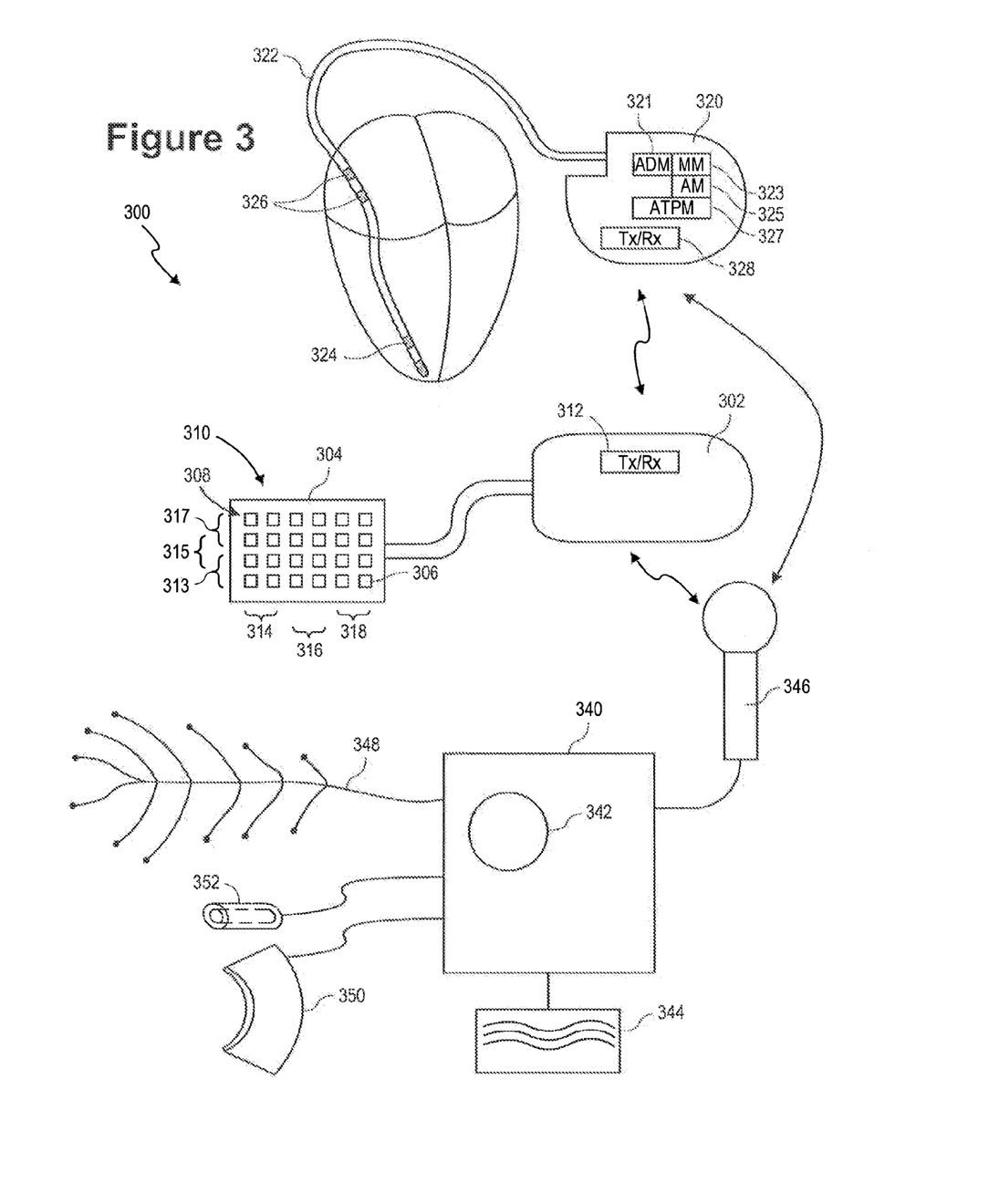
FIG. 3 illustrates a block diagram of an exemplary system that may be implemented in accordance with an embodiment.

FIG. 3 illustrates a block diagram of an exemplary system 300 that may be implemented in accordance with an embodiment. The system 300 includes an NS device 302 that is coupled to an NS lead 304. As one example, the NS lead 304 includes electrodes 306 that are arranged in a two dimensional array of rows 308 and columns 310. The electrodes 306 delivery NS therapies based on the current operating NS configuration. Optionally, other NS lead configurations may be used.

The NS device 302 will activate different combinations of the electrodes 305, such as to electronically shift a placement where and configuration at which an AET-NS therapy is delivered on a particular spinal region. For example, during NS configurations #1, #2 and #3, different electrode column combinations 314, 316 and 318. respectively, may be active. By moving between NS configurations, and thus active electrode column combinations 314, 316 and 318, the AET-NS therapy can be delivered at different lateral or longitudinal positions along the vertebra relative to a lateral reference point. Similarly, the active electrode row combinations 313, 315 and 317 could be switched to shift a position of the AET-NS therapy in a vertical direction up or down relative to a vertical reference point on a vertebra.

Optionally, a separate implantable medical device (IMD) 320 may be provided. The IMD 320 may be a pacemaker, ATP device, ICD device, CRT device, other CRM device such as subcutaneous AF monitor, or other device configured to sense and/or deliver stimulus to cardiac tissue. The IMD 320 is coupled to at least one lead 322 that has a distal end that is configured to be inserted into one or more chambers of the heart. For example, the lead 322 may include a distal end with one or more electrodes 324 inserted into the right ventricle. The lead 322 may also include one or more electrodes 326 located in the right atrium. The lead 322 represents one example and in no way is intended to limit the present invention. Optionally, more or different leads may be included, such as leads with electrodes proximate to the LA and/or LV. The electrodes 324 and 326 sense RP and/or SS signals and may also deliver pacing and/or high voltage stimulus to the heart tissue. The IMD 320 includes a transmitter/receiver (Tx/Rx) 328 that is configured to communicate with the transmitter/receiver (Tx/Rx) 312 in the NS device 302. The Tx/Rx 328 may convey, among other things, RP and/or SS signals sensed at the IMD 320 to the NS device 302, The IMD 320 detects and analyzes the RP and/or SS signals sensed by the electrodes 324, 326 to identify onset, change, and/or termination of an AE.

An external device 340 is shown in FIG. 3. The external device 340 may be a home monitoring device, a Holter monitor worn by the patient, an external IMD or NS programmer, an ECG monitor and the like.

The external device 340 includes a display 342, an input keyboard 344, and an antenna 346 used to communicate with the NS device 302 and the IMD 320. A surface electrode set 348 is joined to the external device 340 to collect RP and/or SS signals. Optionally, a blood pressure cuff 350 and blood oxygen sensor 352 may be coupled to the external device 340 to sense blood pressure and blood oxygen content, respectively, in connection with deriving RP and SS signals. The external device 340 may transmit RP and/or SS signals from the surface electrode set 348, the blood pressure cuff 350 and/or blood oxygen sensor 352 to the NS device 302 through the antenna 346.

The external device 340 may include an arrhythmia detection module, a measurement module, an analysis module and an ATP module. Optionally, the external device 340 may also perform the respiratory pattern analysis and/or the sleep stage analysis to analyze signals from a respiration sensor and signals from sleep stage sensors. The external device 340 may also select the AET-NS therapy based on the respiratory pattern and/or the sleep stage. When the external device 340 selects an AET-NS therapy, the external device 340 transmits instructions to change the AET-NS therapy and/or each new AET-NS therapy.

As described herein, an NS device is used to deliver AET-NS therapy. Optionally, the IMD or an external device may be used to deliver AET-NS therapy. Hence, the terms "spinal column stimulus", "SCS" or "NS module" are used herein to collectively refer to any software function, device or system that delivers AET-NS therapy, such as a separate NS device, an IMD configured to deliver AET-NS therapy, an external device configured to deliver AET-NS therapy and the like.

In accordance with at least one implementation, a patient or physician may initially calibrate the system by programming one or more AET-NS therapies, respiratory pattern criteria (to designate when therapy is warranted), sleep stage criteria (to designate when therapy is warranted) and the like. The patient then utilizes the NS device 150 for a period of time to determine whether the programmed therapy(ies) are effective, namely are able to terminate AE through paresthesia delivery without fully waking the patient up. When the patient determines that the AET-NS therapy is not effective (e.g., is not terminating AE or wakes up the patient during some or all apnea episodes), then the patient or physician may reprogram the NS device by adjusting the AET-NS therapy(ies). For example, an external device in-home patient care system may permit the patient to change various therapy parameters such as amplitude, left or right side stimulation, stimulation of an inferior or superior body segment, and the like. Each morning, the patient may review, through the external device, AE information from the prior night's sleep, such as the number of AE, the duration of each AE, whether an initial AET-NS therapy terminated the AE, how many different AET-NS therapies were needed to terminate the AE and the like. From this information the patient may decide to increase or decrease the therapy strength.

Optionally, the patient may review, through the external device, sleep stage information from the prior night's sleep, such as i) which sleep stage the patient was in when the AE occurred and the AET-NS therapy delivered, ii) in response to therapy delivery, how did the patient's sleep stage change, and the like. The patient may choose to deliver a first select AET-NS therapy when the patient is experiencing light sleep (e.g., associated with theta brain waves). The patient may choose to deliver a second different select AET-NS therapy when the patient is experiencing deep sleep (e.g., associated with delta brain waves).

Figure 4:
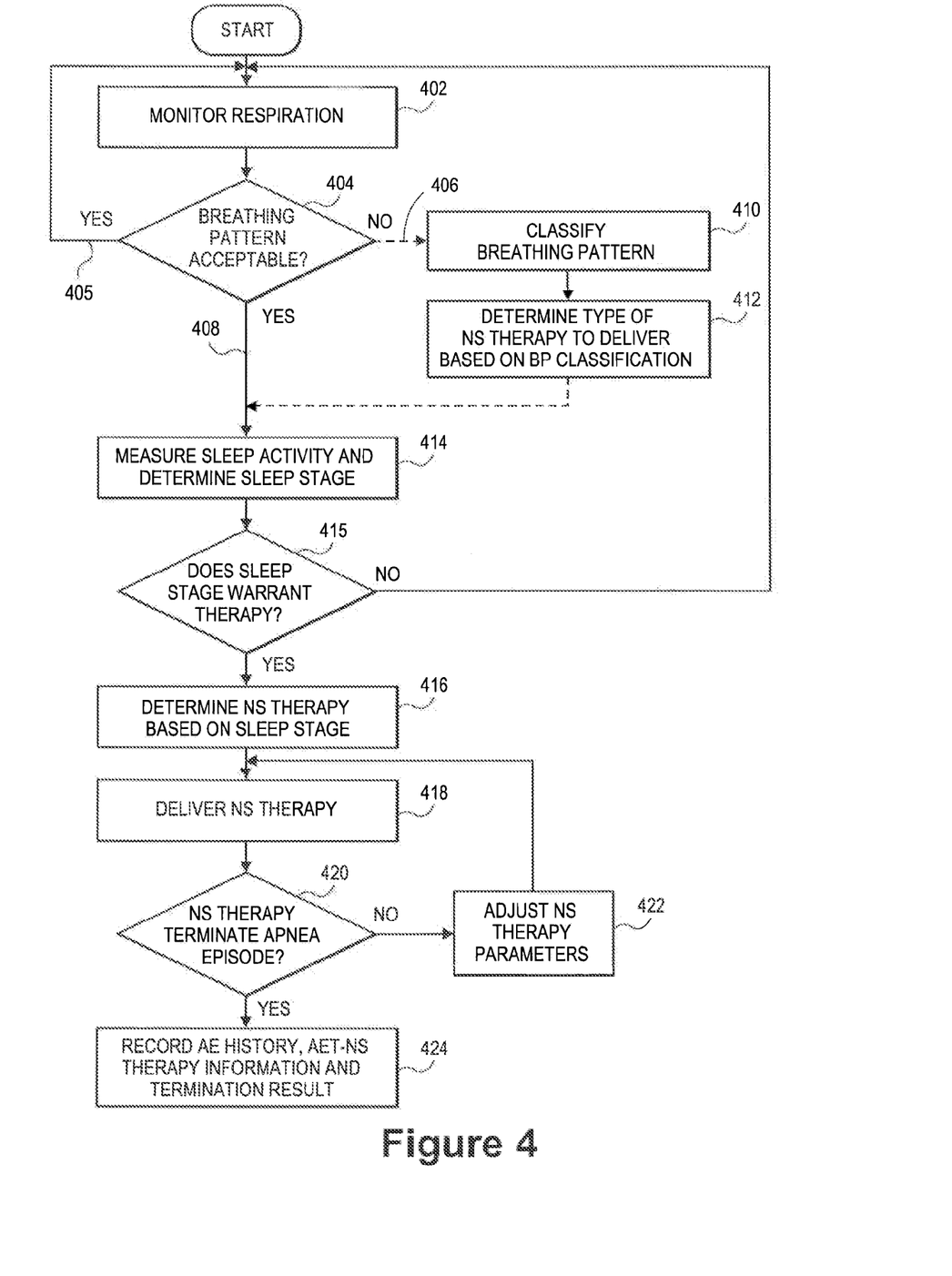
FIG. 4 illustrates a method carried out in accordance with an embodiment for delivering apnea episode terminating neuro-stimulation (AET-NS) therapy to treat sleep apnea.

FIG. 4 illustrates a method carried out in accordance with an embodiment for delivering apnea episode terminating neuro-stimulation (AET-NS) therapy to treat sleep apnea. As explained herein, in accordance with certain aspects of the method, one of several types of AET-NS therapy may be delivered based on one or more of the respiratory pattern of the patient and/or the sleep stage experienced by the patient at the time that the apnea episode occurs. The AET-NS therapy may be adjusted automatically or manually by the patient and/or by a physician. The method may automatically adjust the AET-NS therapy based on an effectiveness of one or more prior AET-NS therapy, based on whether the AET-NS therapy wakes up the patient, based on whether the AET-NS therapy causes the patient to change to a different sleep state, and/or based on other criteria. The method may afford manual adjustment by permitting the patient and/or a physician to remotely reprogram the NS device. For example, the patient may have a home monitoring device (e.g., located near the bed) that communicates with the NS device. Among other things, the home monitoring device may record/download various information from the NS device such as when each AE occurs, as well as other physiologic conditions of the patient during each AE (e.g., sleep state, respiratory pattern, time when AE begins/ends, duration of AE, a count of the number of AEs during one sleep cycle or one evening, and the like). As another example, a physician may utilize an external programmer device to communicate with the NS device and record/download various types of information from the NS device such as when each AE occurs, as well as other physiologic conditions of the patient.

Upon reviewing the information recorded/downloaded by the external programmer or home monitoring device, the physician and/or patient may adjust the operating parameters of the NS device such as to increase or decrease the AET-NS therapy. As used throughout the present application, the terms "increase" and "decrease" when used to describe the AET-NS therapy refer to changing values of one or more parameters of the AET-NS therapy and are measured relative to a severity of paresthesia as experienced by the patient.

Beginning at 402, the method monitors the patient's respiration. The method may be activated automatically based on the time of day, or based on sensors that detect that the patient is lying down. Optionally, the method may be activated when the NS device 150 detects that a sleep stage monitor or sensor has been turned on or is within wireless communications range of a transceiver in the NS device 150. Optionally, the NS device 150 may be turned on by the patient when the patient is going to bed. Various types of sensors may be used to monitor respiration. For example, the sensor may be an accelerometer, EGM signals from an implantable cardiac device, an external motion sensor (e.g., placed on the chest or elsewhere on the patient), a satellite implantable sensor to monitor respiration or another sensor known to measure respiration. The sensors collection respiration signals representative of the patient respiratory pattern over a predetermined period of time (e.g., a few seconds, one or more cardiac cycles, and the like). The predetermined period of time may be set by a physician or determined automatically by the device while in operation based on past breathing activity.

At 404, the method analyzes the respiration signals to determine whether the patient respiratory pattern is acceptable or unacceptable. For example, the respiration signals may include characteristics that are indicative of a respiration rate and/or tidal volume associated with breathing. When one or both of the respiration rate and/or tidal volume drop below a select/normal threshold or range for a sleeping individual, the method may determine that the respiratory pattern is not acceptable. Optionally, other characteristics of the respiratory pattern may be monitored instead or in addition to the respiration rate and tidal volume, and used in the determination at 404. An unacceptable respiratory pattern may represent a low respiration rate, excessively long delays or interruptions (e.g., that exceed a threshold) between breaths, fewer than a select number of breaths in a select period of time and the like. When the respiratory pattern is acceptable, then the method determines that the patient does not warrant delivery of an AET-NS therapy and flow returns along 405 to start the process over. When the respiratory pattern is unacceptable, then the method determines that the patient warrants delivery of an AET-NS therapy and thereafter flow may advance along one of alternative paths, namely 406 and 408.

The path 406 represents an optional path along which the method first classifies the type of respiratory pattern. At 410, the method classifies the measured respiratory pattern. Various types of respiratory patterns may be detected and indicative of different conditions or states of apnea. For example, the morphology of the respiration signal from the sensor may be analyzed for one or more features of interest to classify the respiratory pattern. For example, the feature(s) of interest in the respiratory pattern morphology may represent the peak to peak amplitude, the interval between peaks, a number of zero crossings, the maximum slope (positive or negative), a number of peaks or valleys, an area under the curve or other characteristic of the respiration signals.

Optionally, at 410, the respiration signal(s) may be compared to one or more predetermined RP templates, where each RP template is associated with a corresponding unique sleep breathing disorder or corresponding stage within a sleep disorder. The measured respiration signals may be correlated to the RP templates and a respiratory pattern classification declared based on the RP template that exhibits the best (or closest) correlation to the measured respiration signals.

Once the respiratory pattern is classified at 410, flow moves to 412, where the method determines the type of AET-NS therapy that should be delivered. The AET-NS therapy to be delivered is based, at least in part, on the type of respiratory pattern that is classified. For example, a lookup table or other correlation may be recorded in memory to associate each respiratory pattern classification with an AET-NS therapy. As one example, each respiratory pattern classification may be associated with a unique AET-NS therapy. As another example, subsets of respiratory pattern classifications may be associated with a common AET-NS therapy.

Optionally, the AET-NS therapies may be programmed over time by a patient and/or physician. For example, a patient may learn through various AE and trial AET-NS therapies, that when a patient is exhibiting a select respiratory pattern (e.g., short shallow breathes, an uneven breathes pattern with breaths spaced apart by a certain number of seconds) the past most effective AET-NS therapy was configured to target one or both lower leg extremities. Alternatively, the patient may learn through various AE and trial AET-NS therapies, that the past most effective AET-NS therapy should be configured to target the persons hands or arms. Optionally, a patient may learn through various AE and trial AET-NS therapies, that when a patient is sleeping on one side or the other side (or on the patient's back or stomach), the past most effective AET-NS therapy may vary. For example, when sleeping on the left side, the AET-NS therapy may be configured to target the lower leg extremity of the left leg (or the right leg). Optionally, when sleeping on one side, the AET-NS therapy may be configured to target a select ear or facial cheek (e.g., the side that is directed upward and not on the pillow). Optionally, when the patient is sleeping on his/her back, the AET-NS therapy may be found to be most effective when configured to target the nose, one hand, one arm or one foot. Once the AET-NS therapy is determined at 412, flow returns to 414.

Optionally, the operations at 410 and 412, and the path 406, may be omitted entirely. Instead, flow may advance directly from 404 to 414 when the respiratory pattern is determined to be unacceptable. As one example, when flow moves from 404 to 414, a single predetermined therapy may be preprogrammed by a physician or may be automatically determined based on past AET-NS therapy delivery and other factors.

At 414, the method monitors the patient's sleep activity. Various types of sensors may be used to monitor sleep activity. For example, the sensor may be an electroencephalogram (EEG) which monitors brain waves, or an electrooculograph (EOG) which monitors eye movement, and/or another type of sensor that has been found to provide measurements of a physiologic stage correlated to sleep stage. Analysis of EEG and EOG data allows identification of all sleep stages. For example, the sensors contain a detecting element, amplifiers and filters, an AD converter, and a microprocessor. The sensors may be integrated into the NS device, or coupled via wire to the NS device or communicate wirelessly with the NS device. As one example, the sensors may utilize a Bluetooth link to the NS device, to the home monitoring device, and/or to the external programmer device. The EEG and/or EOG sensor could be used for periodic examination or continuous examination. Optionally, the sensor may include sensors to monitor EGM signals (such as from an implantable cardiac device), an external motion sensor (e.g., placed on the chest or elsewhere on the patient). The sensors collection sleep stage signals representative of the patient sleep stage over a predetermined period of time (e.g., a few seconds, one or more cardiac cycles, and the like). The predetermined period of time may be set by a physician or determined automatically by the device while in operation based on past breathing activity.

At 414, the method also analyzes the sleep activity signals to determine what sleep stage the patient is experiencing. There are five stages of sleep and each distinct stage serves a different purpose. In general, a person may cycle through all five stages several times. The first stage is the lightest stage of sleep, the transition phase. Stage 1 is also the last stage before waking up. The second stage of sleep is still considered light sleep, when brain activity starts to slow down, as well as the heart rate and breathing. The body temperature may fall a little. The third stage represents the start of deep sleep, also known as slow wave sleep. During stage 3, brain waves are slow "delta waves," although there may still be short bursts of faster brain activity (also known as beta-waves). When a person is awakened suddenly during stage 3, the person may be groggy and confused, and find it difficult to focus at first.

The stage 4 represents the stage in which a person experiences the deepest sleep of the night. The brain only exhibits delta-wave (slow wave) activity, and it is difficult to wake someone up when they are in Stage 4 of sleep. Normally, stages 3 and 4 may last anywhere from 5-15 minutes each, but the first deep sleep of the night is more likely to be an hour or so. The fifth stage of sleep is when dreams occur. It is also referred to as "active sleep" or REM sleep, which stands for the rapid eye movements that characterize Stage 5. During REM sleep, blood flow, breathing, and brain activity increases. As an example, the EEG sensor signals may show that a brain is about as active as it is when a person is awake. Another aspect of stage 5 sleep is that the muscles in our arms and legs will go through periods of paralysis.

Normally, the first period of REM sleep of the night may begin about 90 minutes after a person drifts off, and lasts for about 10 minutes. As the night passes, the periods of REM sleep become longer, with the final episode lasting around an hour.

At 414, the method determines which sleep stage the patient is experiencing based on the sleep stage activity signals. Various types of sleep stage patterns may be detected and indicative of the different conditions or sleep stages. For example, the morphology of the sleep stage signal from the sensor may be analyzed for one or more features of interest to classify the sleep stage. For example, the feature(s) of interest in the sleep stage activity signal morphology may represent the peak to peak amplitude, the interval between peaks, a number of zero crossings, the maximum slope (positive or negative), a number of peaks or valleys, an area under the curve or other characteristic of the sleep stage signals.

Optionally, at 414, the sleep stage signal(s) may be compared to one or more predetermined sleep stage templates, where each sleep stage template is associated with a corresponding unique sleep stage. The measured sleep stage signals may be correlated to the sleep stage templates and a respiratory pattern classification declared based on the sleep stage template that exhibits the best (or closest) correlation to the measured sleep stage signals.

Once the sleep stage is classified at 414, flow moves to 415, where the method determines whether the sleep stage warrants therapy. For example, a physician or patient may determine that, when the patient is in stages 1-2 of sleep that no AET-NS therapy should be delivered when an apnea episode occurs. When the method determines that no therapy is warranted, flow moves to point A at the beginning of the method. Alternatively, at 415, when the method determines that therapy is warranted, flow moves to 416.

At 416, the method determines the type of AET-NS therapy that should be delivered. The AET-NS therapy to be delivered is based, at least in part, on the sleep stage that was identified in 414. For example, the AET-NS therapy may be preprogrammed by the patient or a physician to a first AET-NS therapy when in sleep state 1, a second AET-NS therapy when in sleep state 2, a third AET-NS therapy when in sleep state 4, a fourth AET-NS therapy when in sleep state 4, and a fifth AET-NS therapy when in sleep state 5. Optionally, the AET-NS therapy may be preprogrammed to a first AET-NS therapy when in a first select number of sleep states (e.g., sleep states 1-3), and a second AET-NS therapy when in a second select number of sleep states (e.g., sleep states 4-5). For example, the first AET-NS therapy may deliver a low energy stimulation that is configured to cause a tingling sensation in one or both feet, while a second AET-NS therapy may deliver a higher energy stimulation (relative to the first AET-NS therapy) that is configured to cause a tingling or even a slight pain sensation along a lower portion of one or both legs. The determination at 416 may afford management of AET-NS therapies to avoid the patient waking up with a start, feeling groggy and/or disoriented.

Optionally, the AET-NS therapy may be preprogrammed to induce paresthesia at a first location when in a select number of sleep states (e.g., sleep states 1-3), and to induce paresthesia at a second location when in a select number of sleep states (e.g., sleep states 4-5). Alternatively, the AET-NS therapy may be preprogrammed by the patient or a physician to induce paresthesia at a first location when in sleep state 1, to induce paresthesia at a second location when in sleep state 2, to induce paresthesia at a third location when in sleep state 4, to induce paresthesia at a fourth location when in sleep state 4, and to induce paresthesia at a fifth location when in sleep state 5. Alternatively, the AET-NS therapy may be preprogrammed by the patient or a physician to induce paresthesia at a first set of locations when in certain sleep states, and to induce paresthesia at a second set of locations when in other sleep states.

Optionally, the AET-NS therapy determined, at 416, may be based in part on the sleep state and in part on the respiratory pattern (if determined at 410 and 412). For example, each sleep state may have a subset of potential AET-NS therapies associated therewith depending upon the respiratory pattern. A lookup table or other correlation may be recorded in memory to associate each respiratory pattern classification and each sleep state with a corresponding AET-NS therapy. As one example, each sleep state, may have 4-5 potential different respiratory pattern classifications for which the patient and/or physician may be record unique AET-NS therapies. As another example, multiple sleep states and subsets of respiratory pattern classifications may be associated with a common AET-NS therapy.

Optionally, the AET-NS therapies may be programmed over time by a patient and/or physician. For example, a patient may learn through various AE and trial AET-NS therapies, that when a patient is exhibiting a select sleep state the past most effective AET-NS therapy is configured to target one or both lower leg extremities. Alternatively, the patient may learn through various AE and trial AET-NS therapies, that the past most effective AET-NS therapy should be configured to deliver a certain level of stimulation or target the person's hands or arms. Optionally, a patient may learn through various AE and trial AET-NS therapies, that when a patient is sleeping on one side or the other side (or on the patient's back or stomach), and in sleep stages 4 or 5, the past most effective AET-NS therapy may vary as compared to when the patient is in sleep stage 1 or 2.

At 418, the method delivers the AET-NS therapy. The AET-NS therapy may be defined by various parameters. The parameters may include electrode location, electrode combinations, pulse amplitude, pulse width, pulse frequency, intervals between successive groups of pulses, a number of pulses in each group, and the like.

The method of FIG. 4 is iterative such that the AET-NS therapy may be delivered several times each night while the patient is sleeping. The parameters may be adjusted between successive iterations through FIG. 4. During each iteration through FIG. 4, the AET-NS therapy may be adjusted based on various factors, such as the success of past AET-NS therapy to terminate specific individual apnea episodes. The AET-NS therapy parameters may be ramped up/down. For example, the amplitude and/or frequency of the AET-NS therapy may be progressively increased upon failure of an AET-NS therapy to terminate an apnea episode.

In one example, the AET-NS therapy may begin by delivering (in one location) NS pulses utilizing standard parameters and then, the method may simultaneously turn on AET-NS therapy at a second location. The combined NS therapies may result in cessation of the apnea episode without fully waking the patient.

At 420, the method again monitors the patient respiration to determine whether the AET-NS therapy(ies) were successful to terminate the apnea. Optionally, the method may utilize a second type of monitor to monitor the patient state of awareness to determine whether the AET-NS therapy caused the patient to wake up. For example, the state of awareness sensors may represent EEG sensors to monitor whether the patient reaches full wakefulness.

At 420, the method monitors the respiration and determines whether the apnea episode persists. If respiration returns to normal, the method is done and the method resets to continue to monitor for the next AE. The determination at 420 is based on new respiratory pattern signals that are collected by the sensors that monitor respiration at 402. If the respiratory pattern signals indicate that the apnea episode persists and therefore the AET-NS therapy failed to terminate the AE, then a more aggressive AET-NS therapy may be delivered. Hence, flow moves to 422.

At 422, the AET-NS therapy parameters are adjusted to one or more different programmed stimulation pulses. For example, the adjustment may include changing one or more of electrode location, electrode combinations, pulse amplitude, pulse width, pulse frequency, intervals between successive groups of pulses, a number of pulses in each group, and the like. The adjustment may include increasing the stimulation strength by a select amount (e.g., 0.5V, 1.0V). Optionally, the method may step through a series of AET-NS therapies that are programmed by the patient and/or a physician. Once the AET-NS therapy is adjusted at 422, flow returns to 418 and the new AET-NS therapy is delivered.

Optionally, the operations at 420 and 422 may be omitted entirely such that the flow advances from 418 directly to 424. Alternatively, during each iteration through the method of FIG. 4, the operations at 420 and 422 may only be performed once, twice or a set number of times (even if the AE is not terminated) to avoid entering a loop that continues an excessive number of adjustments. Once the AE is terminated or a limit is reached for the number of iterations through 420 and 422, then flow moves to 424.

At 424, the NS device records, downloads or otherwise wirelessly transmits to the home monitoring device various information from the NS device. For example, the NS device may record the AE history, AET-NS therapy information, and termination results. The AE history may include information such as when each AE occurs, as well as other physiologic conditions of the patient during each AE (e.g., sleep state, respiratory pattern, time when AE begins/ends, duration of AE, a count of the number of AEs during one sleep cycle or one evening, and the like). The AET-NS therapy information may include the parameter values for the therapy as delivered, when the therapy was delivered, whether adjustments were made to the therapy, how many therapy attempts were made and the like. The termination results may indicate whether the AET-NS therapy was successful in terminating the AE, what physiologic state the patient was in or changed to upon termination of the AE. and the like. For example, the method may record the sleep state of the patient after the AE is terminated. Optionally, a physician may utilize an external programmer device to communicate with the NS device and record/download various types of information.

In accordance with methods and systems described herein the NS device 150 may download from the NS device 150 to an external device various information such as but not limited to at least one of a number of AE occurring in a select period of time, a duration of at least one AE, a number of times that the AET-NS therapy is delivered, a count of a success rate of the AET-NS therapy, and a history of the sleep stages in which the AET-NS therapy was delivered. One or more of the external devices described herein include a display to present at least one of an AE history information and AET-NS therapy history information to a patient or physician and permitting the patient or physician to adjust the AET-NS therapy based on the at least one of an AE history information and AET-NS therapy history information. The methods described herein may include automatically or manually (under patient or physician control) iteratively adjusting the AET-NS therapy in order to determine a select AET-NS therapy that induces a sufficient level of paresthesia to terminate the AE without fully awakening the patient.

Examples of AE history information include when each AE occurs, as well as other physiologic conditions of the patient during each AE (e.g., sleep state, respiratory pattern, time when AE begins/ends, duration of AE, a count of the number of AEs during one sleep cycle or one evening, a number of AE occurring in a select period of time, a duration of at least one AE, The AET-NS therapy information may include the parameter values for the therapy as delivered, when the therapy was delivered, whether adjustments were made to the therapy, how many therapy attempts were made, include a number of times that the AET-NS therapy is delivered, a count of a success rate of the AET-NS therapy, and the like). The termination results may indicate whether the AET-NS therapy was successful in terminating the AE, what physiologic state the patient was in or changed to upon termination of the AE, and the like. For example, the method may record the sleep state of the patient after the AE is terminated.

The term "wake up" or "woke up" as used throughout refers to a patient that is substantially fully awake and aware. It is recognized that embodiments herein encompass AET-NS therapies that fully wake up the patient, while other embodiments herein encompass AET-NS therapies that only partially wake up the patient. Embodiments herein further encompass AET-NS therapies that simply cause the patient to transition from one sleep stage to another sleep stage, or maintain the patient in the same sleep stage before and after delivery of the AET-NS therapy.

Figure 5:
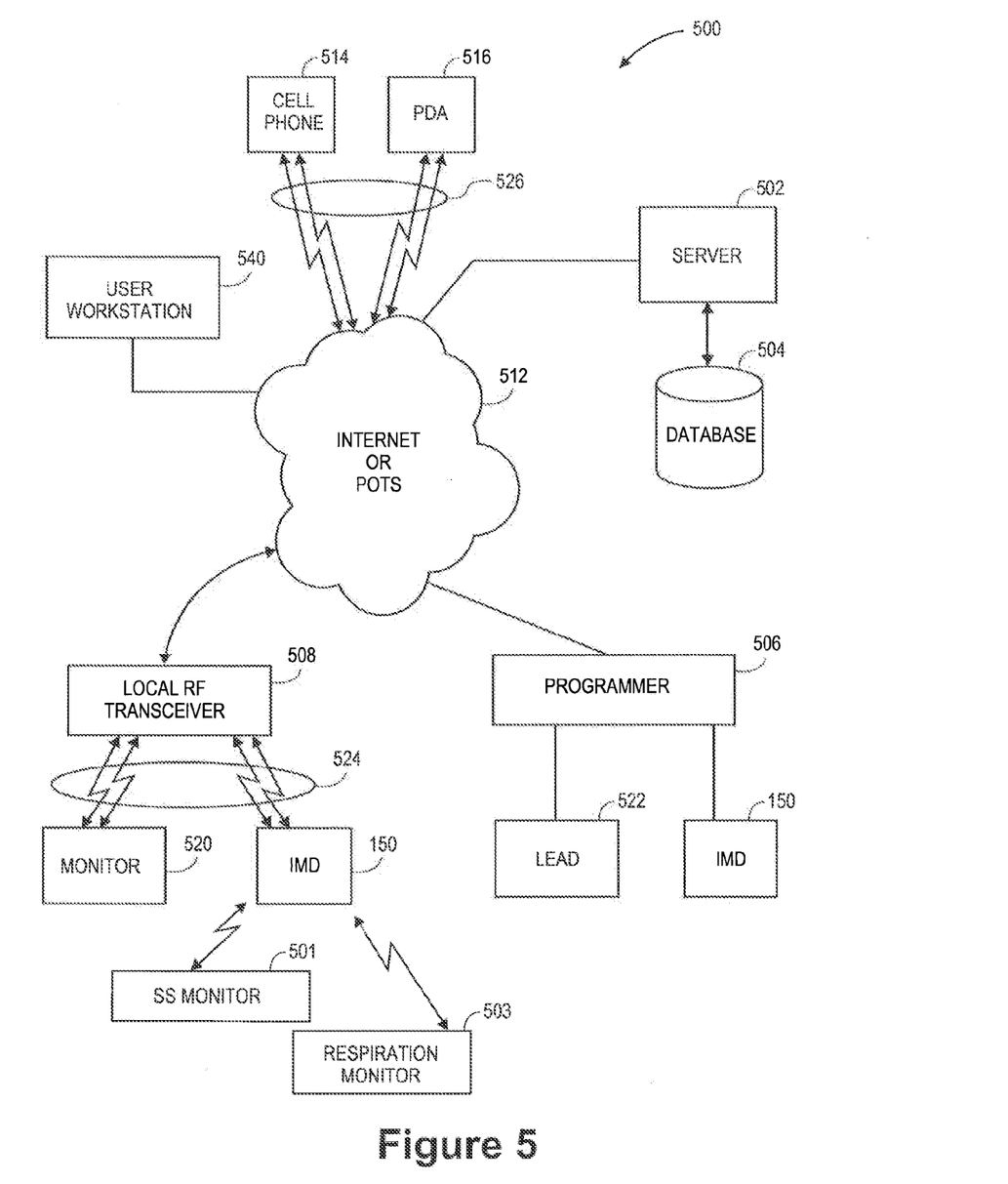
FIG. 5 illustrates a distributed processing system in accordance with one embodiment.

FIG. 5 illustrates a distributed processing system 500 in accordance with one embodiment. The distributed processing system 500 includes a server 502 connected to a database 504, a programmer 506, a local RF transceiver 508 and a user workstation 510 electrically connected to a communication system 512. Any of the processor-based components in FIG. 5 (e.g., workstation 510, cell phone 514, PDA 516, server 502, programmer 506, NS device 150) may perform the RP and SS signal analysis, and AET-NS therapy adjustments discussed herein.

The communication system 512 may be the internet, a voice over IP (VoIP) gateway, a local plain old telephone service (POTS) such as a public switched telephone network (PSTN), a cellular phone based network, and the like. Alternatively, the communication system 512 may be a local area network (LAN), a campus area network (CAN), a metropolitan area network (MAN), or a wide area network (WAM). The communication system 512 serves to provide a network that facilitates the transfer/receipt of information such as RP and/or SS signals and other information discussed herein.

The server 502 is a computer system that provides services to other computing systems over a computer network. The server 502 controls the communication of information. The server 502 interfaces with the communication system 512 to transfer information between the programmer 506, the local RF transceiver 508, the user workstation 510 as well as a cell phone 514 and a personal data assistant (PDA) 516 to the database 504 for storage/retrieval of records of information. On the other hand, the server 502 may upload raw RP and/or SS signals from an implanted lead 522, surface ECG unit 522 or the NS device 150 via the local RF transceiver 508 or the programmer 506. The programmer 506, user workstation 510, cell phone 514, PDA 516, external device 600 and the like include a display configured to present some or all of the information discussed herein to the patient or physician. For example, the display may present at least one of an AE history information and AET-NS therapy history information to a patient or physician and permitting the patient or physician to adjust the AET-NS therapy based on the at least one of an AE history information and AET-NS therapy history information.

The database 504 stores the various information discussed herein, such as the RP and SS signals measured, AET-NS therapies programmed and delivered, the history logs regarding the AE episodes, therapies that were delivered, changes in RP and SS before and after delivery of a therapy and the like, for a single or multiple patients. The information is downloaded into the database 504 via the server 502 or, alternatively, the information is uploaded to the server from the database 504. The programmer 506 is similar to the external device 600 and may reside in a patient's home, a hospital, or a physician's office. The programmer 506 interfaces with the lead 522 and the NS device 150. The programmer 506 may wirelessly communicate with the NS device 150 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 506 to the NS device 150. The programmer 506 is able to acquire respiratory pattern and sleep stage signals from the surface respiration or sleep stage monitor 520. The programmer 506 interfaces with the communication system 512, either via the internet or via POTS, to upload the information acquired from the monitor 520, the lead 522 or the NS device 150 to the server 502. The NS device 150 may be connected wired or wireless to one or both of the SS monitor 501 and 503.

The local RF transceiver 508 interfaces with the communication system 512 to upload the information discussed herein to the server 502. In one embodiment, the monitor 520 and the NS device 150 have a bi-directional connection 524 with the local RF transceiver 508 via a wireless connection. The local RF transceiver 508 is able to acquire RP and/or SS signals from the surface of a person. On the other hand, the local RF transceiver 508 may download stored RP and/or SS signal waveforms and the like, from the database 504 to the monitor 520 or the NS device 150.

The user workstation 510 may interface with the communication system 512 via the internet or POTS to download RP and/or SS signals waveforms, templates, AE history, information downloaded from the NS device, AET-NS therapies, detection thresholds and the like via the server 502 from the database 504. Alternatively, the user workstation 510 may download raw data from the monitors 520, lead 522 or NS device 150 via either the programmer 506 or the local RF transceiver 508. Once the user workstation 510 has downloaded the RP and/or SS signals, and other information the user workstation 510 may process the information in accordance with one or more of the operations described herein. The user workstation 510 may download the information and notifications to the cell phone 514, the PDA 516, the local RF transceiver 508, the programmer 506, or to the server 502 to be stored on the database 504. For example, the user workstation 510 may communicate data to the cell phone 514 or PDA 516 via a wireless communication link 526.

Figure 6:
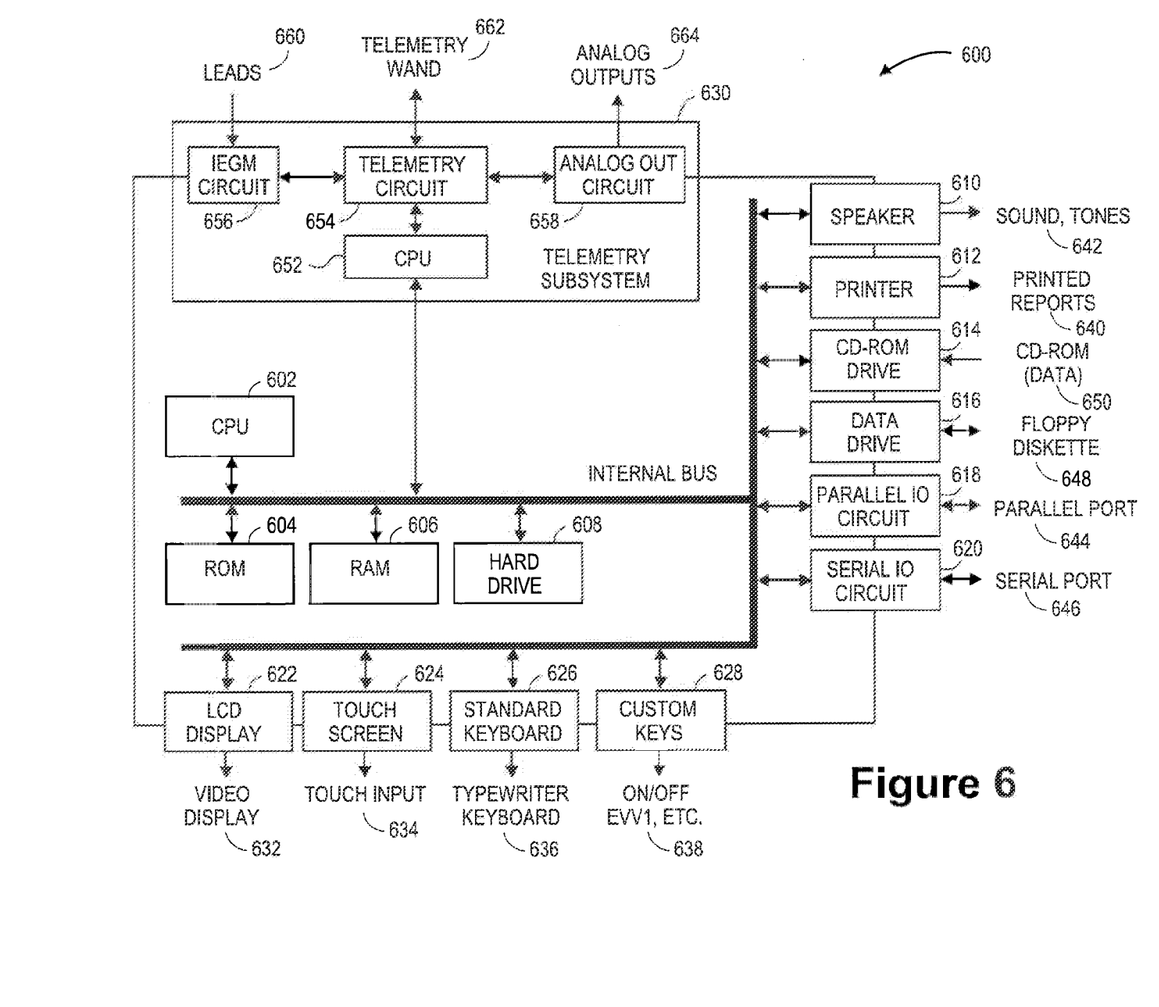
FIG. 6 illustrates a functional block diagram of the external device that is operated in accordance with the processes described herein and to interface with implantable medical devices as described herein.

FIG. 6 illustrates a functional block diagram of the external device 600 that is operated in accordance with the processes described herein and to interface with implantable medical devices as described herein. The external device 600 may be a workstation, a portable computer, an IMD programmer, a PDA, a cell phone and the like. The external device 600 includes an internal bus that connects/interfaces with a Central Processing Unit (CPU) 602, ROM 604, RAM 606, a hard drive 608, the speaker 610, a printer 612, a CD-ROM drive 614, a floppy drive 616, a parallel I/O circuit 618, a serial I/O circuit 620, the display 622, a touch screen 624, a standard keyboard connection 626, custom keys 628, and a telemetry subsystem 630. The internal bus is an address/data bus that transfers information between the various components described herein. The hard drive 608 may store operational programs as well as data, such as waveform templates and detection thresholds.

The CPU 602 typically includes a microprocessor, a microcontroller, or equivalent control circuitry, designed specifically to control interfacing with the external device 600 and with the NS device 150. The CPU 602 performs the COI measurement process discussed above. The CPU 602 may include RAM or ROM memory, logic and timing circuitry, state machine circuitry, and I/O circuitry to interface with the NS device 150. The display 622 (e.g., may be connected to the video display 632). The touch screen 624 may display graphic information relating to the NS device 150. The display 622 displays various information related to the processes described herein. The touch screen 624 accepts a user's touch input 634 when selections are made. The keyboard 626 (e.g., a typewriter keyboard 636) allows the user to enter data to the displayed fields, as well as interface with the telemetry subsystem 630, Furthermore, custom keys 628 turn on/off 638 the external device 600. The printer 612 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a memory stick. The CD-ROM drive 614 accepts CD ROMs 650.

The telemetry subsystem 630 includes a central processing unit (CPU) 652 in electrical communication with a telemetry circuit 654, which communicates with both a RP circuit 656 and an analog out circuit 658. The circuit 656 may be connected to leads 660. The circuit 656 is also connected to the implantable leads 114, 116 and 118 to receive and process RP and/or SS signals as discussed above. Optionally, the RP and/or SS signals sensed by the leads 114, 116 and 118 may be collected by the NS device 150 and then transmitted, to the external device 600, wirelessly to the telemetry subsystem 630.

The telemetry circuit 654 is connected to a telemetry wand 662. The analog out circuit 658 includes communication circuits to communicate with analog outputs 664. The external device 600 may wirelessly communicate with the NS device 150 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 600 to the NS device 150.

It is to be understood that the above description is intended to be illustrative and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments.

Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A neural stimulation (NS) device for treating apnea episodes, comprising:
 a respiration sensor configured to detect a respiratory pattern of a patient and to output respiratory pattern signals;
 a respiration analysis (RA) module configured to determine when the respiratory pattern signals indicate an apnea episode (AE);
 a sleep stage (SS) sensor configured to detect a sleep stage that the patient is experiencing and to output a SS signal;
 a sleep state analysis (SSA) module configured to identify when the sleep stage warrants therapy based on the SS signal; and
 a therapy module configured to deliver an apnea episode terminating neuro-stimulation (AET-NS) therapy, when the AE is detected and the sleep stage warrants therapy, wherein the AET-NS therapy is configured to terminate the AE.

2. The NS device of claim 1, wherein the therapy module determines a type of AET-NS therapy to be delivered based on the sleep stage that was detected, wherein the AET-NS therapy is configured to shift the patient from one sleep stage to a different sleep stage.

3. The NS device of claim 1, wherein the respiration sensor detects a new respiratory pattern following delivery of a prior AET-NS therapy, the respiration analysis module is configured to determine whether the prior AET-NS therapy successfully terminated the AE, the therapy module configured to adjust the AET-NS therapy and deliver a new AET-NS therapy when the prior AET-NS therapy was not successful in terminating the AE.

4. The NS device of claim 1, wherein the therapy module is configured to automatically increase the AET-NS therapy when the AET-NS therapy does not successfully terminate the AE.

5. The NS device of claim 1, wherein the therapy module is configured to automatically decrease the AET-NS therapy when the AET-NS therapy causes excessive paresthesia that wakes up the patient.

6. The NS device of claim 1, wherein the RA module is configured to determine whether the AET-NS therapy caused paresthesia sufficient to end the AE, and the SSA module is configured to determine when the AET-NS therapy did not wake up the patient, the therapy module configured to adjust the AET-NS therapy based on whether the AET-NS therapy ended the AE and whether the AET-NS therapy woke up the patient.

7. The NS device of claim 1, further comprising a communications input configured to communicate with an external device, the external device having a user input configured to permit the patient or a physician to enter program information to increase and decrease the AET-NS therapy.

8. The NS device of claim 1, further comprising a transceiver to transmit from the NS device, to an external device, at least one of a number of AE occurring in a select period of time, a duration of at least one AE, a number of times that the AET-NS therapy is delivered, a count of a success rate of the AET-NS therapy, and a history of the sleep stages in which the AET-NS therapy was delivered.

9. The NS device of claim 1, further comprising an external device with a display configured to present at least one of an AE history information, AET-NS therapy history information or termination results to a patient or physician and permitting the patient or physician to adjust the AET-NS therapy based on the at least one of an AE history information, AET-NS therapy history information or termination results.

10. The NS device of claim 1, wherein the therapy module is configured to iteratively adjust the AET-NS therapy, under control of the patient or physician, in order to determine a select AET-NS therapy that induces a sufficient level of paresthesia to terminate the AE without fully awakening the patient.

11. A neural stimulation (NS) device for treating apnea episodes, comprising:
 a respiration sensor configured to detect a respiratory pattern of a patient and to output respiratory pattern signals;
 a respiration analysis (RA) module configured to determine when the respiratory pattern signals indicate an apnea episode (AE);

a sleep stage (SS) sensor configured to detect a sleep stage that the patient is experiencing and to output a SS signal;

a sleep state analysis (SSA) module configured to identify when the sleep stage warrants therapy based on the SS signal; and a therapy module configured to deliver stimulation pulses to a nerve system of a patient when the AE is detected and the sleep stage warrants therapy, wherein the stimulation pulses are configured to terminate the AE.

12. The NS device of claim 11, wherein the stimulation pulses are configured to induce a sufficient level of paresthesia sufficient to terminate the AE without fully awakening the patient.

13. The NS device of claim 11, wherein the therapy module is configured to:

induce a first level of paresthesia by delivering stimulation pulses based on a first sleep stage being detected; and induce a second level of paresthesia by delivering stimulation pulses based on a second sleep stage being detected, wherein the first and second levels of paresthesia are different.

14. The NS device of claim 11, wherein the therapy module is configured to induce paresthesia at one or more first locations based on a first sleep stage being detected and induce paresthesia at one or more second locations based on a second sleep stage being detected, wherein the first and second locations are different.

15. The NS device of claim 11, wherein the therapy module is configured to automatically increase at least one of an amplitude, frequency, and location of the stimulation pulses when the stimulation pulses do not successfully terminate the AE.

16. The NS device of claim 11, wherein the therapy module is configured to automatically decrease at least one of an amplitude, frequency, and location of the stimulation pulses when the stimulation pulses cause excessive paresthesia that wakes up the patient.

17. The NS device of claim 11, wherein the RA module is configured to determine whether the stimulation pulses caused paresthesia sufficient to end the AE, and the SSA module is configured to determine when the stimulation pulses did not wake up the patient, the therapy module configured to adjust the stimulation characteristics of the stimulation pulses based on whether the stimulation pulses ended the AE and whether the AET-NS therapy woke up the patient.

18. The NS device of claim 11, further comprising an external device with a display configured to present at least one of an AE history information, stimulation pulses history information or termination results to a patient or physician and permitting the patient or physician to adjust the stimulation pulses based on the at least one of an AE history information, AET-NS therapy history information or termination results.

19. The NS device of claim 11, wherein the therapy module is configured to iteratively adjust the stimulation pulses, under control of the patient or physician, in order to determine a select stimulation pulses that induces a sufficient level of paresthesia to terminate the AE without fully awakening the patient.

* * * * *